United States Patent [19]

Stähle et al.

[11] 4,125,620
[45] Nov. 14, 1978

[54] 2-[(2',6'-DISUBSTITUTED-PHENYL)-IMINO]-IMIDAZOLIDINES AND SALTS THEREOF

[75] Inventors: Helmut Stähle; Herbert Köppe; Werner Kummer, all of Ingelheim am Rhein; Wolfgang Hoefke, Budenheim, all of Fed. Rep. of Germany

[73] Assignee: Boehringer Ingelheim GmbH, Ingelheim am Rhein, Fed. Rep. of Germany

[21] Appl. No.: 850,780

[22] Filed: Nov. 11, 1977

Related U.S. Application Data

[63] Continuation-in-part of Ser. No. 720,991, Sep. 7, 1976, abandoned, which is a continuation-in-part of Ser. No. 615,930, Sep. 23, 1975, abandoned.

[30] Foreign Application Priority Data

Oct. 1, 1974 [DE] Fed. Rep. of Germany ....... 2446758

[51] Int. Cl.² .................. A61K 31/415; C07D 233/46
[52] U.S. Cl. ................................... 424/273 R; 548/315
[58] Field of Search ..................... 548/315; 424/273 R

[56] References Cited

U.S. PATENT DOCUMENTS

| | | | |
|---|---|---|---|
| 2,899,426 | 8/1959 | Bloom | 548/315 |
| 2,938,038 | 5/1960 | Hirt et al. | 548/315 |
| 3,027,370 | 3/1962 | Bindler | 548/315 |
| 3,190,802 | 6/1965 | Zeile et al. | 548/315 |
| 3,236,857 | 2/1966 | Zeile et al. | 548/315 |
| 3,296,077 | 1/1967 | Berg | 548/315 |
| 3,595,961 | 7/1971 | Stähle et al. | 548/315 |
| 3,622,579 | 11/1971 | Stähle et al. | 548/315 |
| 3,773,767 | 11/1973 | Stähle et al. | 548/315 |
| 3,931,216 | 1/1976 | Franzmair | 548/315 |

FOREIGN PATENT DOCUMENTS 772,626 11/1967 Canada.
1,034,938 10/1962 United Kingdom.
1,180,766 2/1970 United Kingdom.

*Primary Examiner*—Natalie Trousof
*Attorney, Agent, or Firm*—Hammond & Littell

[57] ABSTRACT

Compounds of the formula

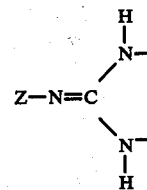

wherein Z is
  2-ethyl-6-methyl-phenyl,
  2,6-di-trifluoromethyl-phenyl,
  2-chloro-6-trifluoromethyl-phenyl or
  2-fluoro-6-trifluoromethyl-phenyl, and non-toxic, pharmacologically acceptable acid addition salts thereof; the compounds as well as the salts are useful as hypotensives.

7 Claims, No Drawings

2-[(2',6'-DISUBSTITUTED-PHENYL)-IMINO]-IMIDAZOLIDINES AND SALTS THEREOF

This is a continuation-in-part of copending application Ser. No. 720,991 filed Sept. 7, 1976, now abandoned, which in turn is a continuation-in-part of application Ser. No. 615,930 filed Sept. 23, 1975, now abandoned.

This invention relates to novel 2-[(2', 6'-disubstituted-phenyl)-imino]-imidazolidines and non-toxic acid addition salts thereof, as well as to various methods of preparing these compounds.

More particularly, the present invention relates to a novel class of 2-phenylimino-imidazolidines represented by the formula

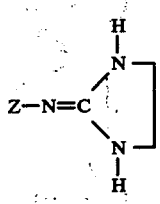

(I)

wherein Z is
2-ethyl-6-methyl-phenyl,
2,6-di-trifluoromethyl-phenyl,
2-chloro-6-trifluoromethyl-phenyl or
2-fluoro-6-trifluoromethyl-phenyl,
and non-toxic, pharmacologically acceptable acid-addition salts thereof.

The compounds embraced by formula I may be prepared by the following methods:

Method A

By reacting a compound of the formula

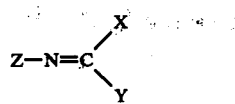

(II)

wherein
Z has the same meanings as in formula I, and
X and Y, which may be identical to or different from each other, are each halogen (preferably chlorine), sulfhydryl, alkylthio of 1 to 4 carbon atoms, alkoxy of 1 to 4 carbon atoms, hydroxyl, amino or nitroamino,
or a salt thereof, with ethylenediamine or a salt thereof.

Examples of the types of compounds embraced by formula II are isocyanide dihalides (especially isocyanide dichlorides), thioureas, O-alkyl-ureas, S-alkyl-thioureas, guanidines, carbamic acid esters, thiocarbamic acid chlorides, alkylthiocarbamic acid chlorides and nitroguanidines.

The reaction is performed at a temperature between 0° and 200° C, depending upon the reactivity of substituents X and Y, and advantageously in the presence of a polar protic, polar aprotic or non-polar solvent medium. However, if substituents X and Y are sufficiently reactive, the reaction may also be carried out at elevated temperatures in the absence of a solvent medium. In those cases where one or both of X and Y are halogen, the presence of an acid binding agent during the reaction is recommended. The reaction time depends largely upon the reactivity of the reactants and may vary between a few minutes and several hours.

Method B

By reacting a compound of the formula $$Z-NH-C\equiv N$$ (III)

wherein Z has the same meanings as in formula I, with ethylenediamine or a salt thereof.

This reaction must be performed at elevated temperatures between 60° and 180° C, but the presence of a solvent medium is not required. It is advantageous, however, to provide the ethylenediamine reactant in excess over and above the stoichiometric amount required.

Method C

By reacting an aniline of the formula $$Z-NH_2$$ (IV)

wherein Z has the same meanings as in formula I, with the compound of the formula

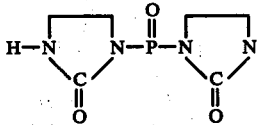

(V)

The reaction must be performed at elevated temperature between 80° and 180° C, advantageously in the presence of a non-polar, inert solvent medium.

Method D

By cyclizing a urea or thiourea derivative of the formula

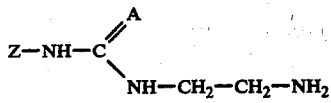

(VI)

wherein
Z has the same meanings as in formula I, and
A is oxygen or sulfur.

The cyclization is effected by heating the starting compound of the formula VI to a temperature between 120 and 160° C. The presence of a solvent medium is not required.

Method E

By reacting an aniline of the formula IV with an imidazoline of the formula

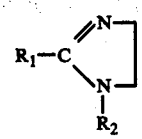

(VII)

wherein
$R_1$ is a nucleophilic exchangeable substituent, such as halogen (preferably chlorine), methylthio, methoxy or hydroxyl, and
$R_2$ is hydrogen or aliphatic acyl.

$R_1$ is hydroxyl, it is advantageous that $R_2$ be carboxylic acyl, such as acetyl. In that case the reaction between the aniline of the formula IV and the 1-acyl-imidazoline-2-ol is advantageously performed in the presence of phosphorus oxychloride at moderately elevated temperatures, such as about 50° C. The required reaction time may be anywhere from several hours to several days. The preparation of a compound of the formula I from the resulting reaction product requires a subsequent removal of the acyl group by hydrolysis, which is most advantageously effected by refluxing the 1-acylated reaction product with a lower alkanol, such as methanol.

The reaction of an aniline of the formula IV with a 2-methylthio-2-imidazoline or 2-chloro-2-imidazoline of the formula VIII requires higher temperature (100° to 180° C). The presence of a solvent medium is not required, but may be provided, if so desired. Suitable solvents are primarily polar protic or polar aprotic solvents.

Method F

By reacting a carbodiimide of the formula $$Z - N = C = N - Z \qquad (VIII)$$

wherein Z has the meanings previously defined, with ethylenediamine or a salt thereof.

This reaction is advantageously carried out in the presence of an inert solvent medium, such as benzene, at room temperature and, after distilling off the solvent, heating the reaction mixture to an elevated temperature of about 100° to 200° C.

Method G

For the preparation of a compound of the formula I wherein Z is halo-substituted phenyl, by exchanging the amino-substituent in a [2-(2'-amino-phenyl)-imino]-imidazolidine of the formula

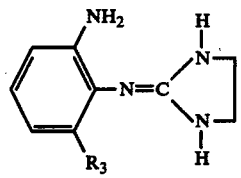

wherein $R_3$ is fluorine or chlorine, for a fluoro- or chloro-substituent. The exchange is carried out by means of the known Sandmeyer Reaction.

2,6-disubstituted anilines of the formula IV, which are also new, may be prepared by either of the two methods illustrated by the following schematic reaction sequences, where R and R' represent the 2- and 6-substituents on the phenyl moiety defined in conjunction with variable Z in formula I:

Reaction sequence No. 1

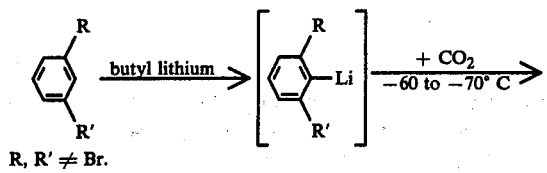

R, R' ≠ Br.

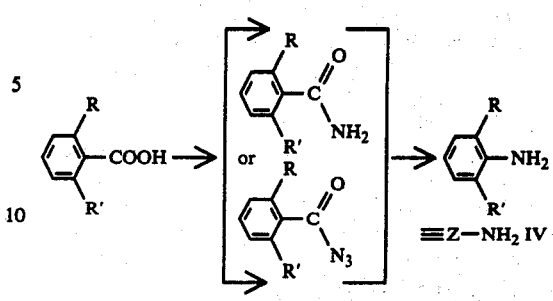

Reaction sequence No. 2

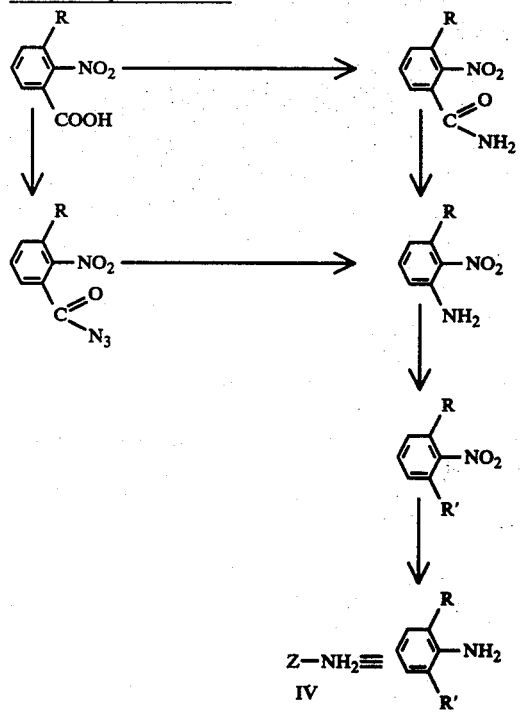

In the synthesis according to reaction sequence No. 1, not only the desired 2,6-disubstituted benzoic acid compounds, but also isomers thereof are formed, and these are most advantageously separated by column chromatography on silicagel.

The synthesis of 2,6-di-trifluoromethyl-phenyl lithium, an intermediate step in the preparation of 2,6-di-trifluoromethyl-aniline pursuant to reaction sequence No. 1, is described by G. Hallas et al. in J. Soc. Dyers and Colourists 86, 200 (1970).

The intermediates or starting compounds used in the other methods described above are all derived from the anilines of the formula IV and may be prepared by methods described in the literature. For instance, the carbodiimides of the formula VIII and the isocyanide dichlorides of the formula II may be prepared from the anilines of the formula IV as follows:

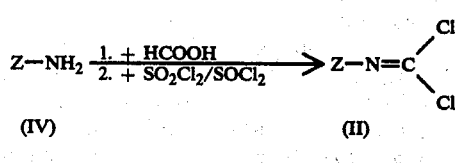

-continued

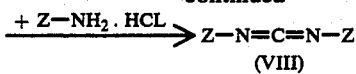

The compounds embraced by formula I are organic bases and therefore form addition salts with inorganic or organic acids. Exammples of non-toxic, pharmacologically acceptable acid addition salts are those formed with hydrochloric acid, hydrobromic acis, hydroiodic acid, hydrofluoric acid, sulfuric acid, phosphoric acid, nitric acid, acetic acid, propionic acid, butyric acid, caproic acid, valeric acid, oxalic acid, malonic acid, fumaric acid, lactic acid, tartaric acid, citric acid, malic acid, benzoic acid, p-hydroxy-benzoic acid, p-aminobenzoic acid, phthalic acid, cinnamic acid, salicylic acid, ascorbic acid, methanesulfonic acid, ethanephosphonic acid, 8-chlorotheophylline or the like.

The following examples illustrate the present invention and will enable other skilled in the art to understand it more completely. It should be understood, however, that the invention is not limited solely to the particular examples given below.

EXAMPLE 1

2-[(2'-Ethyl-6'-methyl-phenyl)-imino]-imidazolidine by method A

A mixture consisting of 322 gm (0.96 mol) of N-(2-ethyl-6-methyl-isothiouronium hydroiodide and 96 ml of ethylenediamine was heated for 20 minutes at 150° C on an oil bath. Thereafter, the excess, unreacted ethylenediamine was evaporated in vacuo, the viscous residue was taken up in a little methanol, and the raw base was precipitated from the solution with aqueous 50% potassium hydroxode accompanied by addition of water ,while cooling on ice. The aqueous phase was decanted, the oily base was dissolved in chloroform, and the resulting solution was dried over anhydrous magnesium sulfate and then evaporated in vacuo. The residue was dissolved in dilute hydrochloric acid, and the resulting solution was fractionally extracted with ether at various, gradually increasing pH-values (addition of dilute sodium hydroxide). The thin-layer chromatographically pure fractions were combined and evaporated to dryness in vacuo. For further purification the evaporation residue was chromatographed on Al$_2$O$_3$, using chloroform as the eluant, yielding 32.4 gm (16.6% of theory) of the compound of the formula

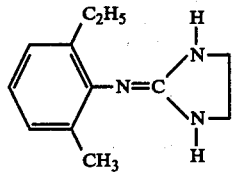

which was of high purity and had a melting point of 134°–136° C.

EXAMPLE 2

2-[(2', 6'-Di-triflfuoromethyl-phenyl)-imino]-imidazolidine and its hydrochloride by method A N-(2', 6'-Di-trifluoromethyl-phenyl)-isocyanide dichloride was prepared by reaction sequence No. 1 from 1,3-di(trifluoromethyl)-benzene via 2,6-di(trifluoromethyl)-benzoic acid (m.p. 136-°–138° C), 2,6-di-(trifluoromethyl)-benzamide (m.p. 200°–202° C), 2,6-di-(trifluoromethyl)-aniline and 2,6-di-(trifluoromethyl)-formanilide (m.p. 179°–181° C).

1.25 gm (0.004 mol) of the isocyanide dichloride thus prepared were added a mixture of 2.7 gm of ethylenediamine and 15 ml of absolute ether at 10° C, while stirring. After all of the isocyanide dichloride had been added, the reaction mixture was allowed to warm to room temperature and was then stirred at that temperature for 30 minutes more. Thereafter, the reaction mixuture was evaporated to dryness in vacuo, the residue was dissolved in dilute hydrochloric acid, and the resulting solution was extracted twice with ether at a pH of about 5.5 for purification purposes. Thereafter, the aqueous solution of 2-[(2', 6'-di-trifluoromethylphenyl)-imino]-imidazolidine hydrochloride thus obtained was made alkaline with 5 N sodium hydroxide while simultaneously adding petroleium ether thereto. A crystalline substance separated out which was collected by suction filtration, washed with a little water and petroleum ether, and dried. 360 mgm (30.2% of theory) of still slightly impure base having a melting point of 170°–174° C were obtained. For further purification the raw base was chromatographed on silicagel, using a mixture of methanol:acetone:chloroform (6:3:15) as the eluant, yielding very pure 2-[(2', 6'-di-trifluoromethyl-phenyl)-imino]-imidozolidine having a melting point of 177°–178° C.

EXAMPLE 3

2-[(2'-chloro-6'-trifluoromethyl-phenyl)-amino]-imidazoline and its hydrochloride by method A (a) N-(2-chloro-6-trifluoromethyl-phenyl)-isocyanide dichloride was synthesized by means of reaction sequence No. 1 described above from 3-chloro-benzotrifluoride via the intermediates 2-chloro-6-trifluoromethyl-benzoic acid (m.p. 120°–123° C), 2-chloro-6-trifluoromethyl-aniline (an oil), and 2-chloro-6-trifluoromethyl-formanilide (m.p. 167°–170° C).

(b) A mixture consisting of 9 gm of N-(2-chloro-6-trifluoromethyl-phenyl)-isocyanide dichloride, 21.6 ml of ethylenediamine (10-fold excess) and 100 cc of absolute ether was stirred for 30 minutes at 10° C. Thereafter, the reaction mixuture was evaporated in vacuo, the oily residue was dissolved in dilute hydrochloric acid, the resulting solution was extracted twice with ether, and the acid aqueous phase was purified with activated twice with ether, and the acid aqueous phase was purified with activated charcoal. After filtering off the charcoal, the filtrate was fractionally extracted with ether at different, gradually increasing pH-values (addition of sodium hydroxide). The thin-layer chromatographically pure ethereal fractions containing the free base, 2-[(2-chloro-6'-trifluoromethyl-phenyl)-imino]-imidazolidine, were combined, dried and then admixed with ethereal hydrochloric acid until acid reaction to Congo Red. The precipitate formed thereby was collected and dried, yielding 3.2 gm (32.9% of theory) of the hydrochloride which was a white crystalline substance having a melting point of 277°–279° C. It was readily soluble in water and lower alkanols.

EXAMPLE 4

Using a procedure analogous to that described in Example 3, 44.9% of theory of 2-[(2'-fluoro-6'-trifluoromethylphenyl)-imino]-imidazolidine hydrochloride, m.p. 262°–264° C, was obtained by means of reaction sequence No. 1 described above via the intermediates 2-fluoro-6-trifluoromethyl-benzoic acid (m.p. 81°–84° C), 2-fluoro-6-trifluoromethyl-aniline (an oil) and 2-fluoro-6-trifluoromethyl-formanilide (m.p. 116°–118° C), followed by reaction of the corresponding isocyanide dichloride with ethylenediamine.

The compounds of the present invention, that is, those embraced by formula I above and their non-toxic, pharmacologically acceptable acid addition salts, have useful pharmacodynamic properties. More particularly, the compounds of this invention exhibit hypotensive activities in warm-blooded animals, such as cats and dogs, and are therefore useful for the treatment of hypertonia.

2-Phenylimino imidazolidines have for long time attracted considerable interest because of their outstanding pharmacological and therapeutic properties. Many compounds of this type have therefore been described in the prior art, such as in Belgian Pat. Nos. 623,305; 653,933; 687,636; 687,657 and 705,944. Various processes for the preparation of 2-phenylimino-imidazolidines are also disclosed in the prior art.

In accordance with recent investigations, it has been determined that, among the structural characteristics of 2-phenylimino-imidazolidines which are responsible for a central, α-adrenergic stimulating effect, their configuration is of decisive importance. Thus, structure-activity investigations have shown that only those derivatives of 2-phenylimino-imidazolidine exhibit good hypotensive activities whose phenyl and imidazolidine rings are in planar configuration with respect to each other. Under these conditions the free rotation of the phenyl ring about the single C—N bond is hindered, and the two rings are in perpendicular or substantially perpendicular planes with respect to each other.

In the case of 2-phenylimino-imidazolidines, an aplanar configuration can be achieved by attaching substituents to the ortho-positions of the aromatic moiety, that is, by forming compounds of the formula

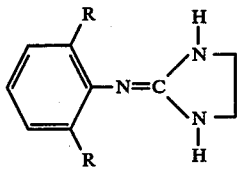

where R and R' are blocking atoms or atom groups which hinder the free rotation of the phenyl ring about the single C—M bond and thus the possibility of a coplanar configuration of the two rings with respect to each other.

For pharmaceutical purposes the compounds of the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective hyposentive dosage unit of the compounds according to the present invention is from 0.0016 to 1.3 mgm/kg body weight, preferably 0.0083 to 0.5 mgm/kg body weight.

The following examples illustrate a few pharmaceutical dosage unit compositions comprising a compound of the present invention as an active ingredient and represent the best modes contemplated of putting the invention into practical use. The parts are by weight unless otherwise specified.

EXAMPLE 5

Tablets

The tablet composition is compounded from the following ingredients:

| | |
|---|---|
| 2-[2',6'-Di-trifluoromethyl-phenyl)-imino]-imidazoline | 15 parts |
| Corn starch | 160 parts |
| Secondary calcium phosphate | 250 parts |
| Magnesium stearate | 5 parts |
| Total | 430 parts |

Preparation

The individual ingredients are intimately admixed with each other, the mixture is granulated in conventional manner, and the granulate is compressed into 430 mgm tablets. Each tablet contains 15 mgm of the imidazolidine compound and is an oral dosage unit composition with effective hypotensive action.

EXAMPLE 6

Gelatin capsules

The capsule filler composition is compounded from the following ingredients:

| | |
|---|---|
| 2-[(2', 6'-Di-trifluoromethyl-phenyl)-imino]-imidazolidine | 25 parts |
| Corn starch | 175 parts |
| Total | 200 parts |

Preparation

The ingredients are intimately admixed with each other, and 200 mgm-portions of the mixture are filled into gelatin capsules of suitable size. Each capsule contains 25 mgm of the imidazolidine compound and is an oral dosage unit composition with effective hypotensive action.

EXAMPLE 7

Hypodermic solution

The solution is compounded from the following ingredients:

| | |
|---|---|
| 2-[(2', 6'-Di-trifluoromethyl-phenyl)-imino]-imidazolidine | 1.5 parts |
| Sodium salt of EDTA | 0.2 parts |
| Distilled water     q.s.ad | 100.0 parts |

Preparation

The imidazolidine compound and the EDTA salt are dissolved in a sufficient amount of distilled water, the solution is diluted with additional distilled water to the indicated amount, the resulting solution is filtered until free from suspended particles, and the filtrate is filled into 2 ml ampules under aseptic conditions. The filled ampules are then sterilized and sealed. Each ampule contains 20 mgm of the imidazolidine compound, and its contents are an injectable dosage unit compositon with effective hypotensive action.

Analogous reults are obtained when any one of the other 2-phenylimino-imidazolidines embraced by formula I or a non-toxic, pharmacologically acceptable acid addition salt thereof is substituted for the particular

We claim:
1. A compound of the formula

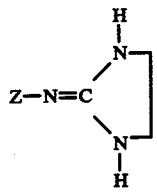

wherein Z is
2-ethyl-6-methyl-phenyl,
2,6-di-trifluoromethyl-phenyl,
2-chloro-6-trifluoromethyl-phenyl or
2-fluoro-6-trifluoromethyl-phenyl,
or a non-toxic, pharmacologically acceptable acid addition salt thereof.

2. A compound of claim 1, which is 2-[(2',6'-ditrifluoromethyl-phenyl)-imino]-imidazolidine or a non-toxic, pharmacologically acceptable acid addition salt thereof.

3. A compound of claim 1, which is 2-[(2'-ethyl-6'-methyl-phenyl)-imino]-imidazolidine or a non-toxic, pharmacologically acceptable acid addition salt thereof.

4. A compound of claim 1, which is 2-[(2'-chloro-6'-trifluoromethyl-phenyl)-imino]-imidazolidine or a non-toxic, pharmacologically acceptable acid addition salt thereof.

5. A compound of claim 1, which is 2-[(2'-fluoro-6'-trifluoromethyl-phenyl)-imino]-imidazolidine or a non-toxic, pharmacologically acceptable acid addition salt thereof.

6. A hypotensive pharmaceutical dosage unit composition consisting essentially of an inert pharmaceutical carrier and an effective hypotensive amount of a compound of claim 1.

7. The method of lowering the blood pressure of a warm-blooded animal in need thereof, which comprises administering to said animal an effective hypotensive amount of a compound of claim 1.

* * * * *

UNITED STATES PATENT OFFICE
CERTIFICATE OF CORRECTION

Patent No. 4,125,620                   Dated November 14, 1978

Inventor(s) HELMUT STÄHLE, HERBERT KÖPPE, WERNER KUMMER and WOLFGANG HOEFKE

It is certified that error appears in the above-identified patent and that said Letters Patent are hereby corrected as shown below:

Column 3, line 1, before "$R_1$" insert --When--.

Column 5, line 29, should read --N-(2-ethyl-6-methyl-phenyl)-

S-methyl-isothiouronium hydroiodide and

96--.

line 35, "hydroxode" should read --hydroxide--.

Column 7, line 50, "C-M bond" should read --C-N bond--.

Column 8, lines 2 and 3, change "The parts are by weight unless otherwise specified.-- to read --The parts are parts by weight unless otherwise specified.-- line 65, "reults" should read -- results --.

Signed and Sealed this

Thirteenth Day of March 1979

[SEAL]

Attest:

RUTH C. MASON
Attesting Officer

DONALD W. BANNER
Commissioner of Patents and Trademarks